United States Patent
Van Patten et al.

(10) Patent No.: US 7,527,956 B2
(45) Date of Patent: May 5, 2009

(54) MODIFIED HUMAN ACID SPHINGOMYELINASE HAVING INCREASED ACTIVITY, AND METHODS FOR MAKING THE SAME

(75) Inventors: Scott M. Van Patten, Ashland, MA (US); Kenneth P. Karey, Bolton, MA (US); Huawei Qiu, Westborough, MA (US)

(73) Assignee: Genzyme Corporation, Cambridge, MA (US)

( * ) Notice: Subject to any disclaimer, the term of this patent is extended or adjusted under 35 U.S.C. 154(b) by 436 days.

(21) Appl. No.: 10/864,981

(22) Filed: Jun. 10, 2004

(65) Prior Publication Data

US 2005/0169906 A1      Aug. 4, 2005

Related U.S. Application Data

(60) Provisional application No. 60/478,124, filed on Jun. 12, 2003.

(51) Int. Cl.
| | |
|---|---|
| *C12N 9/22* | (2006.01) |
| *C12N 15/00* | (2006.01) |
| *C12N 1/20* | (2006.01) |
| *C12P 21/04* | (2006.01) |
| *C12Q 1/00* | (2006.01) |
| *C12Q 1/34* | (2006.01) |
| *C07H 21/04* | (2006.01) |
| *C12Q 1/68* | (2006.01) |

(52) U.S. Cl. ............... 435/199; 435/4; 435/6; 435/69.1; 435/71.1; 435/18; 435/440; 435/252.2; 435/320.1; 536/23.2

(58) Field of Classification Search ............ None
See application file for complete search history.

(56) References Cited

OTHER PUBLICATIONS

Qiu et al. Activation of human acid sphingomyelinase through modification or deletion of C-terminal cysteine. J Biol Chem. Aug. 29, 2003;278(35):32744-52. Epub Jun. 11, 2003.*

Branden et al. Introduction to Protein Structure, Garland Publishing Inc., New York, p. 247, 1991.*

Lansmann, S., et al. (2003). Human acid sphingomyelinase, Eur. J. Biochem. 270, 1076-1088.

Van Wart, H. and Birkedal-Hansen, H. (1990). "The cysteine switch: A principle of regulation of metalloproteinase activity with potential applicability to the entire matrix metalloproteinase gene family", Proc. Natl. Acad. Sci. USA 87, 5578-5582.

Springman, E., et al. (1990). "Multiple modes of activation of latent human fibroblast collagenase: Evidence for the role of a Cys73 active-site zinc complex in latency and a "cystein switch" mechanism for activation" 87, 364-368.

* cited by examiner

*Primary Examiner*—Yong D Pak
(74) *Attorney, Agent, or Firm*—Hamilton, Brook Smith & Reynolds, PC (57) ABSTRACT

Deficiencies in the enzymatic activity of acid sphingomyelinase (ASM) result in Niemann-Pick disease. A variety of modifications which eliminate the activity of the free thiol on the C-terminal cysteine residue of ASM all result in substantially increased specific activity of the enzyme. Methods used to alter the activity of this residue include site-directed mutagenesis to delete or alter the residue, enzymatic degradation of the ASM to remove the residue, copper-promoted dimerization of ASM (via the terminal cysteine residues) and chemical modification of the free thiol group on this residue.

14 Claims, 2 Drawing Sheets

SEQUENCE LISTING

<160> NUMBER OF SEQ ID NOS: 4

<210> SEQ ID NO 1
<211> LENGTH: 629
<212> TYPE: PRT
<213> ORGANISM: Homo sapiens

<400> SEQUENCE: 1

```
Met Pro Arg Tyr Gly Ala Ser Leu Arg Gln Ser Cys Pro Arg Ser Gly
 1               5                  10                  15

Arg Glu Gln Gly Gln Asp Gly Thr Ala Gly Ala Pro Gly Leu Leu Trp
            20                  25                  30

Met Gly Leu Ala Leu Ala Leu Ala Leu Ala Leu Ala Leu Ala Leu Ser
        35                  40                  45

Asp Ser Arg Val Leu Trp Ala Pro Ala Glu Ala His Pro Leu Ser Pro
    50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175
```

-continued

```
Ser Leu Pro Thr Val Pro Lys Pro Pro Lys Pro Ser Pro Pro
            180                 185             190

Ala Pro Gly Ala Pro Val Ser Arg Ile Leu Phe Leu Thr Asp Leu His
        195                 200             205

Trp Asp His Asp Tyr Leu Glu Gly Thr Asp Pro Asp Cys Ala Asp Pro
    210                 215                 220

Leu Cys Cys Arg Arg Gly Ser Gly Leu Pro Pro Ala Ser Arg Pro Gly
225             230                 235                 240

Ala Gly Tyr Trp Gly Glu Tyr Ser Lys Cys Asp Leu Pro Leu Arg Thr
            245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300

Lys Phe Leu Gly Pro Val Pro Val Tyr Pro Ala Val Gly Asn His Glu
305             310                 315                 320

Ser Thr Pro Val Asn Ser Phe Pro Pro Phe Ile Glu Gly Asn His
            325                 330                 335

Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
            355                 360                 365

Leu Ser Pro Tyr Pro Gly Leu Arg Leu Ile Ser Leu Asn Met Asn Phe
            370                 375                 380

Cys Ser Arg Glu Asn Phe Trp Leu Leu Ile Asn Ser Thr Asp Pro Ala
385             390                 395                 400

Gly Gln Leu Gln Trp Leu Val Gly Glu Leu Gln Ala Ala Glu Asp Arg
            405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
            435                 440                 445

Thr Leu Ala Ala Gln Phe Phe Gly His Thr His Val Asp Glu Phe Glu
    450                 455                 460

Val Phe Tyr Asp Glu Glu Thr Leu Ser Arg Pro Leu Ala Val Ala Phe
465             470                 475                 480

Leu Ala Pro Ser Ala Thr Thr Tyr Ile Gly Leu Asn Pro Gly Tyr Arg
            485                 490                 495

Val Tyr Gln Ile Asp Gly Asn Tyr Ser Gly Ser Ser His Val Val Leu
            500                 505                 510

Asp His Glu Thr Tyr Ile Leu Asn Leu Thr Gln Ala Asn Ile Pro Gly
            515                 520                 525

Ala Ile Pro His Trp Gln Leu Leu Tyr Arg Ala Arg Glu Thr Tyr Gly
        530                 535                 540

Leu Pro Asn Thr Leu Pro Thr Ala Trp His Asn Leu Val Tyr Arg Met
545             550                 555                 560

Arg Gly Asp Met Gln Leu Phe Gln Thr Phe Trp Phe Leu Tyr His Lys
            565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys Arg
```

```
                    595                 600                 605
His Leu Met Pro Asp Gly Ser Leu Pro Glu Ala Gln Ser Leu Trp Pro
    610                 615                 620

Arg Pro Leu Phe Cys
625

<210> SEQ ID NO 2
<211> LENGTH: 628
<212> TYPE: PRT
<213> ORGANISM: Homo sapiens

<400> SEQUENCE: 2

Met Pro Arg Tyr Gly Ala Ser Leu Arg Gln Ser Cys Pro Arg Ser Gly
  1               5                  10                  15

Arg Glu Gln Gly Gln Asp Gly Thr Ala Gly Ala Pro Gly Leu Leu Trp
             20                  25                  30

Met Gly Leu Ala Leu Ala Leu Ala Leu Ala Leu Ala Leu Ala Leu Ser
         35                  40                  45

Asp Ser Arg Val Leu Trp Ala Pro Ala Glu Ala His Pro Leu Ser Pro
     50                  55                  60

Gln Gly His Pro Ala Arg Leu His Arg Ile Val Pro Arg Leu Arg Asp
 65                  70                  75                  80

Val Phe Gly Trp Gly Asn Leu Thr Cys Pro Ile Cys Lys Gly Leu Phe
                 85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
    210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300

Lys Phe Leu Gly Pro Val Pro Val Tyr Pro Ala Val Gly Asn His Glu
305                 310                 315                 320

Ser Thr Pro Val Asn Ser Phe Pro Pro Pro Phe Ile Glu Gly Asn His
                325                 330                 335
```

```
Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
            355                 360                 365

Leu Ser Pro Tyr Pro Gly Leu Arg Leu Ile Ser Leu Asn Met Asn Phe
            370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
            405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
            435                 440                 445

Thr Leu Ala Ala Gln Phe Phe Gly His Thr His Val Asp Glu Phe Glu
            450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
            485                 490                 495

Val Tyr Gln Ile Asp Gly Asn Tyr Ser Gly Ser Ser His Val Val Leu
            500                 505                 510

Asp His Glu Thr Tyr Ile Leu Asn Leu Thr Gln Ala Asn Ile Pro Gly
            515                 520                 525

Ala Ile Pro His Trp Gln Leu Leu Tyr Arg Ala Arg Glu Thr Tyr Gly
            530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
            565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys Arg
            595                 600                 605

His Leu Met Pro Asp Gly Ser Leu Pro Glu Ala Gln Ser Leu Trp Pro
            610                 615                 620

Arg Pro Leu Phe
625

<210> SEQ ID NO 3
<211> LENGTH: 629
<212> TYPE: PRT
<213> ORGANISM: Homo sapiens

<400> SEQUENCE: 3

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Ala Leu Ala Leu Ala Leu Ala Leu Ala Leu Ala Leu Ser
            35                  40                  45

Asp Ser Arg Val Leu Trp Ala Pro Ala Glu Ala His Pro Leu Ser Pro
            50                  55                  60

Gln Gly His Pro Ala Arg Leu His Arg Ile Val Pro Arg Leu Arg Asp
65              70                  75                  80
```

-continued

```
Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
    210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300

Lys Phe Leu Gly Pro Val Pro Val Tyr Pro Ala Val Gly Asn His Glu
305                 310                 315                 320

Ser Thr Pro Val Asn Ser Phe Pro Pro Phe Ile Glu Gly Asn His
                325                 330                 335

Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
        355                 360                 365

Leu Ser Pro Tyr Pro Gly Leu Arg Leu Ile Ser Leu Asn Met Asn Phe
    370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Gly His Cys Leu
            420                 425                 430

Lys Ser Trp Ser Trp Asn Tyr Tyr Arg Ile Val Ala Arg Tyr Glu Asn
        435                 440                 445

Thr Leu Ala Ala Gln Phe Phe Gly His Thr His Val Asp Glu Phe Glu
    450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
                485                 490                 495
```

-continued

```
Val Tyr Gln Ile Asp Gly Asn Tyr Ser Gly Ser Ser His Val Val Leu
            500                 505                 510

Asp His Glu Thr Tyr Ile Leu Asn Leu Thr Gln Ala Asn Ile Pro Gly
        515                 520                 525

Ala Ile Pro His Trp Gln Leu Leu Tyr Arg Ala Arg Glu Thr Tyr Gly
    530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
                565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys Arg
            595                 600                 605

His Leu Met Pro Asp Gly Ser Leu Pro Glu Ala Gln Ser Leu Trp Pro
            610                 615                 620

Arg Pro Leu Phe Ser
625

<210> SEQ ID NO 4
<211> LENGTH: 5
<212> TYPE: PRT
<213> ORGANISM: Homo sapiens

<400> SEQUENCE: 4

His Pro Leu Ser Pro
  1               5
```

MODIFIED HUMAN ACID SPHINGOMYELINASE HAVING INCREASED ACTIVITY, AND METHODS FOR MAKING THE SAME

BACKGROUND OF THE INVENTION

Acid Sphingomyelinase, E.C. 3.1.4.12, (ASM) is a lysosomal phosphodiesterase enzyme that hydrolyzes sphingomyelin, a phospholipid storage substance found in the brain, liver, lungs, spleen and lymph-nodes, to ceramide and phosphocholine. Deficiencies in ASM activity result in the inability of the body to break down sphingomyelin, causing a form of the lysosomal storage disease termed Niemann-Pick disease.

Niemann-Pick disease is an inherited autosomal recessive lipid storage disorder characterized by excessive accumulation of sphingomyelin in the lysosomes of cells such as macrophages and neurons, which impairs normal cellular function. Niemann-Pick Type A is a rapidly progressive neurodegenerative disease in infants and typically results in death within two to three years of age. Niemann-Pick Type B results in the enlargement of the liver and spleen, and respiratory distress with death generally ensuing by early adulthood. These two forms of Niemann-Pick disease which are both associated with ASM deficiencies are referred to collectively herein as Niemann-Pick disease. Other types of Niemann-Pick disease, e.g. Type C, do not involve mutations to the ASM gene and are not directly attributable to the function of ASM.

Enzyme replacement therapy is a well-known treatment for lysosomal storage diseases. Enzyme replacement therapy attempts to supplement the deficient enzyme activity with exogenously supplied enzyme. In the case of enzyme replacement therapy for Niemann-Pick disease, the goal would be to enable the affected individual to process sphingomyelin and avoid its buildup within the lysosomes. To be effective, such therapy initially would require a sufficiently large amount of the replacement enzyme to break down the accumulated sphingomyelin as well as continued administration of replacement enzyme to avoid further accumulation of sphingomyelin.

ASM is a glycoprotein with six potential N-glycosylation sites encoded by the amino acid sequence (Schuchman, E. H. et al, (1991) *J. Biol. Chem.*, Vol. 266, 8531-8539). Site-directed mutagenesis studies have shown that at least five of the six sites are utilized (Ferlinz, K., et al., (1997) *Eur. J. Biochem.* Vol. 243, 511-517). This study also found that elimination of the four sites nearest the N-terminus does not disrupt lysosomal targeting, processing, or enzymatic activity. It was shown, however, that removal of the two C-terminal N-glycosylation sites results in either rapid cleavage of the primary translation product or the formation of an inactive ASM precursor (Ferlinz, K., et al., (1997) *Eur. J. Biochem.* Vol. 243, 511-517).

It is generally accepted that a variety of forms of ASM are active in humans, and that these forms are characterized by differing molecular weights and differing glycosylation patterns. ASM has been described in terms of a secretory form found in the circulation, and an intracellular, lysosomal form, both derived from the same gene (Schissel., S. L., et al. (1998) *J. Biol. Chem.* Vol. 273, 18250-18259). The secretory form, obtained either from fetal bovine serum (Spence, M. W., et al. (1989) *J. Biol. Chem.* Vol. 264, 5358-5363) or from various cultured cells (Schissel, S. L., et al. (1996), *J. Biol. Chem.* Vol. 271, 18431-18436), displays increased specific activity in the presence of zinc. Bartelsen et al. also observed copper-dependent activation for recombinant ASM secreted from insect sf21 cells (Bartelsen, O., et al. (1998) *J. Biotechnol*. Vol. 63, 29-40). The lysosomal form of ASM, however, does not require exogenously added zinc for activation and had been referred to as "cation-independent" (Schissel, S. L., et al. (1996), *J. Biol. Chem.* Vol. 271, 18431-18436; Levade, T., (1986) *J. Clin. Chem. Clin. Biochem.* Vol. 24, 205-220). Schissel et al. reported that both the lysosomal and secretory forms can be inactivated by the zinc-specific chelator 1,10-phenanthroline, and thus concluded that both forms require zinc for their enzymatic activity (Schissel., S. L., et al. (1998) *J. Biol. Chem.* Vol. 273, 18250-18259). This suggested that zinc is already tightly associated with the "cation-independent" lysosomal form, making exogenous zinc unnecessary for maximal activity.

The secretory and lysosomal forms of ASM have been shown to have differences in their glycosylation as well as differences in N-termini (Schissel., S. L., et al. (1998) *J. Biol. Chem.* Vol. 273, 18250-18259). With regard to post-translational modifications of these two forms, the lysosomal form of ASM has high mannose-type oligosaccharides, required for phosphorylation and lysosomal targeting, while the secretory form contains complex-type N-linked oligosaccharides. The difference in trafficking pathways for the two forms has been proposed as the reason for their different exposure to cellular zinc and thus their difference in zinc sensitivity (Schissel., S. L., et al. (1998) *J. Biol. Chem.* Vol. 273, 18250-18259). The N-termini of the two forms was shown to be different, due to proteolytic processing of the lysosomal form. Whether differences exist in the C-termini of the two forms has not yet been determined, however C-terminal processing has been reported for several other lysosomal enzymes including acid alpha-glucosidase (Wisselaar., H. A., et al., (1993) *J. Biol. Chem.* Vol. 268, 16504-16511) and cathepsin D (Yonezawa, S., et al., (1988) *J. Biol. Chem.* Vol. 263, 2223-2231; Lloyd, J. B., et al. (1996) *Subcellular Biochemistry* (Harris, J. R., ed) Vol. 27, Plenum Publishing Corp., New York).

It has been proposed that histidine and glutamate residues may participate in metal binding sites within ASM, and comparison of the ASM primary sequence with known zinc metalloproteins suggests as many as seven potential zinc-binding sites (Ferlinz, K., et al., (1997) *Eur. J. Biochem.* Vol. 243, 511-517). The actual stoichiometry of zinc binding and the specific amino acids responsible for coordination of metal ion within ASM remain to be determined. The status of the 17 cysteine residues within ASM, in terms of disulfide linkages and number of free cysteines, is also not well characterized. It has been shown that dithiothreitol (DTT), but not reduced glutathione, inhibits the enzymatic activity of ASM in a concentration-dependent manner (Lloyd, J. B., et al. (1996) *Subcellular Biochemistry* (Harris, J. R., ed) Vol. 27, Plenum Publishing Corp., New York). However, the mechanism of this inactivation is not as yet understood. The inactivation may not be simply due to disulfide reduction, as effects of DTT on protein activity unrelated to disulfide reduction have been reported (Lansmann, S., et al. (2003) *Eur. J. Biochem.* Vol. 270, 1076-1088). In contrast to this inactivation of ASM, lysosomal lipids and the sphingolipid activator protein SAP-C have been shown to stimulate ASM activity (Liu, B., et al. (1997) *J. Biol. Chem.* Vol. 272, 16281-16287).

As mentioned above, enzyme replacement therapy has been proven to be an effective means of treating some lysosomal storage diseases. With respect to ASM, it has been shown that a recombinant form of the enzyme, expressed in CHO cells, has characteristics consistent with the non-recombinant forms including acid pH optimum, sensitivity to sulfhydryl reducing reagents and inhibition by a zinc specific chelator (Schuchman, E. H., et al. (1992) *Genomics* Vol 12, 197-205). During the biochemical characterization of purified recombinant human ASM (rhASM) protein, the present inventors discovered that, unexpectedly, the specific activity of the protein increased when the cell harvests were stored frozen at −20° C. for several weeks. This unexpected activation was identified and, as described herein, was determined to involve the C-terminal cysteine residue of ASM, which is present in a number of active forms of human ASM.

SUMMARY OF THE INVENTION

The present invention relates to methods of increasing the activity of ASMs, particularly with regard to their sphingomyelin hydrolysis activity and to the ASMs with increased activity produced by the methods. Applicants have discovered that modifications of the free cysteine in ASM results in substantially increased activity of ASM toward sphingomylin activity. As set forth herein, a variety of methods of obtaining such ASM's are available to those skilled in this field of protein chemistry.

One aspect of the present invention relates to methods of increasing the sphingomyelin hydrolysis activity of ASM comprising modifying the C-terminal cysteine amino acid residue. In alternative embodiments, the modification can comprise the deletion of the C-terminal cysteine amino acid residue, the substitution of the C-terminal cysteine amino acid residue or the dimerization of the ASM. The loss of the activity of the free thiol group increases the specific activity of the ASM. Thiol protection groups, such as thioether, thioester or an unsymmetrical disulfide can form the attachment compound. Attachment compounds can be reversible or irreversible modifiers of cysteine, such as maleimides. Substitutions of the C-terminal cysteine amino acid residue can be conservative substitutions, such as the substitution of a serine. Dimerization can be accomplished by cross-linking with a sulfide bond.

Another aspect of the invention is directed to modified forms of ASM particularly human ASM and rhASM, wherein the modifications are to the C-terminal cysteine residue. As set forth more fully herein, such modifications can include (a) the deletion of the C terminal cysteine residue and, optionally, additional amino acid residues from the C-terminus, (b) substitution of this cysteine residue by at least one other amino acid residue, (c) chemical modification of this cysteine residue, especially modification of the free thiol group thereof, and (d) dimerization of the ASM protein via the formation of a disulphide bond among the free thiol groups of these terminal cysteine residues. The modified ASM can be SEQ ID NO: 2 or SEQ ID NO: 3. Preferably, such a modification causes the loss of the activity of the free sulfydryl (thiol) group on this residue. These modified forms of ASM according to the present invention exhibit increased specific activity compared to unmodified or wild-type ASM's.

Another aspect of the invention relates to nucleic acid molecules encoding these modified ASMs. This aspect of the invention includes such coding nucleic acids, as well as expression vectors containing them and cells and cell lines which express these modified forms of ASMs.

In another aspect, the invention is directed to a method of treating a subject for an ASM related syndrome comprising administering an effective amount of a modified form of ASM according to the present invention. The modified ASM can be SEQ ID NO: 2 or SEQ ID NO: 3. The syndrome can be lipid histocytosis or Niemann Pick disease.

BRIEF DESCRIPTION OF THE DRAWINGS

FIGS. 2A and 2B are graphs illustrating ASM activation by carboxypeptidase Y (CPY) treatment. ASM was treated with various concentrations of CPY and the resulting loss of C-terminal cysteine was monitored by labeling with Oregon Green® maleimide (OGM).

DETAILED DESCRIPTION OF THE INVENTION

This invention is related to methods of increasing the activity of ASM, typically with regard to their spingomylin hydrolysis activity and to ASMs with increased activity produced by this method. Applicants have discovered that modification of the C-terminal cysteine residue of ASM results in substantially increased activity of ASM toward sphingomyelin hydrolysis. The use of such methods to produced modified ASM with increased activity is advantageous in the treatment of various types of Niemann-Pick disease.

Based on this discovery, the invention provides a method of increasing the activity of ASM, typically the activity of ASM directed toward sphingomyelin hydrolysis. The hydrolysis activity can be increased by modifying the C-terminal cysteine, for example, by deletion, substitution, derivatization or dimerization. As used herein "ASM" is a lysosomal phosphodiesterase enzyme that hydrolyzes sphingomyelin.

ASM has been purified from a variety of sources and has been variously characterized. A form of ASM purified from human urine has been shown to be a 70-kD glycoprotein having an acidic optimal pH (Quintem, L. E., et al., Biochim Biophys Acta 922:323-336).

One allele of the human ASM is available under GEN-BANK accession number NP_000534 and is reproduced herein as SEQ ID NO: 1. This so-called "full-length" version of human ASM consists of 629 amino acid residues, terminating with a cysteine residue designated herein as $CYS^{629}$. However, there is believed to be significant proteolytic processing of the translated protein in the cell. Studies on biosynthesis of ASM indicate a step-wise processing of a 75 kDa pre-pro-protein to an intermediate 72 kDa form inside the ER/Golgi apparatus. The 72 kDa form is further processed to the 70 kDa mature lysosomal enzyme. Smaller forms were also detected in the Golgi and lysosomes. Additionally, it is believed that a variety of polymorphic forms of active human ASM may exist in vivo. Thus, the term "ASM" includes all variations and alleles of SEQ ID NO: 1.

An active form of ASM has been produced recombinantly, and consists of a polypeptide consisting of the 570 amino acid residues of the C-terminus of the "full-length" human ASM of SEQ ID NO: 1. This so-called "rhASM" starts with the sequence His-Pro-Leu-Ser-Pro- at the N-terminus, which is consistent with the sequence of the full-length human ASM starting at $His^{60}$ (SEQ ID NO: 4). For the sake of clarity, all references herein to specific amino acid residues will use position numbers corresponding to those of the full-length human ASM protein, SEQ ID NO: 1. Thus, the C-terminal cysteine residue of rhASM is nevertheless designated as $Cys^{629}$.

The invention is not limited to any particular method or technique of modifying or removing (either physically or functionally) the $Cys^{629}$ residue of an ASM molecule or its pendant active thiol group. For example, and as described more fully herein, ASM dimers can be formed via the formation of a disulfide bond between the terminal cysteine residues of two ASM molecules. Such dimerization effectively modifies the chemical activity of the free thiol groups, which are no longer present. The free thiol of the terminal cysteine residue, alternatively, can be chemically modified by any of a variety of agents, including MMTS (which provides a reversible change to the thiol residue) and Oregon Green® maleimide (OGM) (which imparts an irreversible change). Alternatively, this cysteine residue can be removed enzymatically. For the production of significant quantities of recombinant modified ASM, the sequence of the corresponding cDNA can be designed to eliminate the presence of a C-terminal cysteine with a free thiol group in the resultant product. For example, site-directed mutagenesis can be performed to either modify (e.g. mutate to another amino acid residue, such as serine) or delete (by substitution with a stop codon) this residue. Any method or technique that results in a change to or deletion of this cysteine residue or the thiol group thereof, and which brings about a desired increase in ASM specific activity, can potentially be used.

In a first embodiment, the method of increasing the activity of ASM comprises the deletion of the C-terminal cysteine amino acid residue. The term "C-terminal cysteine" as utilized with ASM refers to the cysteine amino acid residue at the C-terminus of any ASM polypeptide or fragment thereof which exhibits sphingomyelinase activity, particularly such cysteine residues which have a free thiol group. An ASM in which the C-terminal amino acid residue has been deleted is exemplified in SEQ ID NO: 2. As described herein, the deletion can be achieved post-translationally or by translation of a recombinant version of the ASM protein in which the portion encoding the C-terminal cysteine residue has been modified.

In a second embodiment, the method of increasing the activity of ASM comprises the substitution of the C-terminal amino acid residue. The substitution can be a conservative substitution, such as with serine, threonine or alanine. An ASM in which the C-terminal amino acid residue has been deleted is exemplified in SEQ ID NO: 3.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Examples of highly conservative substitutions include valine for leucine, threonine for serine, aspartic acid for glutamic acid and phenylglycine for phenylalanine.

In a third embodiment, the method of increasing the activity of ASM comprises the dimerization of ASM. Preferably, the ASM dimer is cross-linked between the individual ASM C-terminal cysteine residues. More preferably the ASM dimer is cross-linked with a disulfide bond.

In a fourth embodiment, the method of increasing the activity of ASM comprises derivatization of the C-terminal cysteine. Typically, the derivatization comprises the attachment of a compound to the C-terminal cysteine amino acid residue. The compound can comprise a thiol protecting group. Addition of a thiol protecting group forms an S-protected cysteine. Preferably, the thiol protecting group is selected from the group consisting of a thioether, a thioester, or an unsymmetrical disulfide. The compound can also comprise a modifier of cysteine. The modifier can be a reversible or irreversible modifier of cysteine. Preferably, the modifier generates a mixed disulfide with the C-terminal cysteine. Reversible modifiers include for example 5,5'-dithio-bis-(2-nitrobenzoic acid) (Ellman's reagent, DTNB) and methyl methanethiosulfonate (MMTS). Irreversible modifiers include, for example, N-ethylmaleimide (NEM) or OREGON GREEN® 488 maleimide (OGM).

The term "S-protected cysteine" includes a cysteine residue in which the reactivity of the thiol moiety, —SH, is blocked with a protecting group. Suitable protecting groups are known in the art and are disclosed, for example, in T. W. Greene and P. G. M. Wuts, *Protective Groups in Organic Synthesis*, $3^{rd}$ Edition, John Wiley & Sons, (1999), pp. 454-493, the teachings of which are incorporated herein by reference in their entirety. Suitable protecting groups are non-toxic, stable in pharmaceutical formulations and have minimal additional functionality. A free thiol can be protected as a thioether, a thioester, or oxidized to an unsymmetrical disulfide. Typically, the thiol is protected as a thioether. Suitable thioethers include, but are not limited to, S-alkyl thioethers (e.g., $C_1$-$C_5$ alkyl), and S-benzyl thioethers (e.g, Cysteine-S—S-t-Bu). Most typically, the protective group is an alkyl thioether or alternatively, the S-protected cysteine is an S-methyl cysteine.

The invention further relates to modified ASMs which can be produced by the methods of the invention. The term "modified ASM" includes any ASM which has been modified in accordance with the methods of the invention. Modified ASMs include full-length wild-type ASMs which have been modified, or portions thereof. Such ASMs can be produced by modifying a wild-type ASM purified from an appropriate source. Alternatively, such ASMs can be produced as the expression product of a nucleic acid which has been modified according to the methods of the invention. Modified ASMs can also be produced synthetically, and modification can take place either before or after synthesis. Typically, the ASM is of human origin or has a sequence similar to one of human origin, however, ASMs from other species are also contemplated, including but not limited to murine, bovine, rabbit, rat, goat and horse. Modified ASMs include those based on any ASM allele or variant.

The invention further relates to isolated nucleic acid molecules or polynucleotides having nucleotide sequences which encode a modified ASM.

An isolated nucleic acid molecule or nucleotide sequence can include a nucleic acid molecule or nucleotide sequence that is synthesized chemically or by recombinant means. Also, isolated nucleic acid molecules include recombinant DNA molecules in heterologous host cells, as well as partially or substantially purified DNA molecules in solution. The nucleic acid molecules of the present invention can be fused to other coding or regulatory sequences and still be considered isolated. Thus, recombinant DNA contained in a vector is included in the definition of "isolated" as used herein.

The invention further relates to vectors comprising an isolated nucleic acid molecule of the invention operatively linked to a regulatory sequence, as well as to a recombinant host cell comprising the vector. The invention also provides a method for preparing a polypeptide encoded by an isolated nucleic acid molecule described herein (a modified ASM polypeptide), comprising culturing a recombinant host cell of the invention under conditions suitable for expression of said nucleic acid molecule.

Another aspect of the present invention pertains to nucleic acid constructs containing an a nucleic acid molecule described herein. The constructs comprise a vector (e.g., an expression vector) into which a sequence of the invention has been, inserted in a sense or antisense orientation. As used herein, the term "vector" or "construct" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells.

It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The invention further relates to isolated host cells transfected with the vectors as described herein. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., E. coli), insect cells, yeast, or mammalian cells (such as Chinese hamster ovary cells (CHO) or COS cells, human 293T cells, HeLa cells or NIH 3T3. Other suitable host cells are known to those skilled in the art. Vector DNA can be introduced into prokaryotic or eukaryotic cells via conventional transformation or transfection techniques.

The invention further relates to methods of treating a subject in need of treatment for an "ASM related syndrome". ASM related syndromes include any condition related to the capability of ASM to hydrolyze, for example, lysosomal storage diseases such as Niemann-Pick disease Types A and B. The methods of treatment comprise the step of administering to a subject a therapeutically effective amount of a modified ASM. Typically the modified ASM will be one with increased sphingomyelinase hydrolysis activity.

A "subject" is typically a human, but can also be an animal in need of treatment with a modified ASM, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a modified ASM, are subjects with syndromes, diseases and/or conditions that can be treated with modified ASMs to achieve a beneficial therapeutic and/or prophylactic result. A beneficial outcome includes a decrease in the severity of symptoms or delay in the onset of symptoms, increased longevity and/or more rapid or more complete resolution of the disease or condition.

An "effective amount" is the quantity of modified ASM that results in an improved clinical outcome of the condition being treated with the modified ASM compared with the absence of treatment. The amount of modified ASM administered will depend on the degree, severity, and type of the disease or condition, the amount of therapy desired, and the release characteristics of the pharmaceutical formulation. It will also depend on the subject's health, size, weight, age, sex and tolerance to drugs. Those persons skilled in the field of enzyme replacement therapy will be able to design a dosage protocol whereby the modified ASM is administered for a sufficient period of time to achieve the desired therapeutic effect. For example, the modified ASM may be administered at a dosage ranging from 0.1 mg/kg to about 100 mg/kg, preferably from about 0.1 mg/kg to about 10 mg/kg., more preferably from about 0.1 mg/kg to about 2 mg/kg. The modified ASM may be administered, for example, daily, twice weekly, weekly, bi-weekly or monthly via infusion methodology.

The modified ASM can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers should be biocompatible, i.e., non-toxic, non-inflammatory, non-immunogenic and devoid of other undesired reactions at the administration site. Examples of pharmaceutically acceptable carriers include, for example, saline, aerosols, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

Injectable delivery formulations may be administered intravenously or directly at the site in need of treatment. The injectable carrier may be a viscous solution or gel. Delivery formulations include physiological saline, bacteriostatic saline (saline containing about 0.9% mg/mL benzyl alcohol), phosphate-buffered saline, Hank's solution, Ringer's-lactate, or liquids supplemented with albumin, methyl cellulose, or hyaluronic acid. Injectable matrices include polymers of poly (ethylene oxide) and copolymers of ethylene and propylene oxide (see Cao et al., *J. Biomater. Sci.* 9:475 (1998) and Sims et al., *Plast Reconstr. Surg.* 98:843 (1996), the entire teachings of which are incorporated herein by reference). Injectable formulations of recombinant enzymes for the treatment of lysosomal storage diseases are known in the art.

EXAMPLE 1 rhASM Production

Recombinant human ASM protein (rhASM) was produced using Chinese Hamster Ovary (CHO) cells transfected with a vector containing a full-length human ASM cDNA, obtained from the IMAGE Consortium (GenBank Accession AI587087). PCR products were cloned into mammalian expression vectors containing a DHFR selectable marker. Plasmids were sequenced through the entire open reading frame to insure fidelity of the intended sequence. DHFR deficient CHO-DXB11 cells were transfected using lipofectamine (Invitrogen) and selection was carried out in nucleotide deficient media supplemented with 10% dialyzed FBS and 0.2 µM methotrexate (CalBiochem). rhASM expression levels were further boosted by subjecting the uncloned pools to incremental increases in methotrexate concentration. This process generated several unclomed pools that maintained high level rhASM expression upon the withdrawal of methotrexate. The protein was purified from the CHO-conditioned media by conventional orthogonal chromatographic procedures, including hydrophobic interaction and ion exchange steps. The purified rhASM protein was shown to start with His-Pro-Leu-Ser-Pro- (SEQ ID NO: 4) at the N-terminus, corresponding to a 570 amino acid mature protein with signal peptide cleaved between Ala 59 and His 60 of the published human ASM sequence (Quintem, L. E., et al., (1987) *Biochim. Biophys. Acta* Vol. 922, 323-336). This N-terminal sequence is the same as that of the recombinant form of ASM protein produced from insect Sf21 cells (He, X., et al., (1999) *Biochim. Biophys. Acta.* Vol. 1432, 251-264) and CHO cells (Ferlinz, K., et al. (1997) *Eur. J. Biochem.* Vol. 243, 511-517).

EXAMPLE 2

In Vitro Activity Assay rhASM was expressed in a stably transfected recombinant CHO cell line. After harvest of the secreted protein, it was observed that the rhASM activity in the conditioned media increased under certain conditions of storage. A study was carried out to monitor the activity change by incubation at three storage temperatures. It was found that rhASM activity is stable if the harvest media is stored at −80° C., with no change seen over a 160-day period. However, a large increase in ASM activity was seen upon storage of the harvest media at −20° C. There was only a slight increase in activity when the media was stored at 4° C.

To determine whether the increase in activity at −20° C. was due to a change in the specific activity of rhASM itself or whether it might be due to interaction with other molecules (e.g., association with an activator or loss of an inhibitor), rhASM was purified to homogeneity from harvest media. One preparation was made from fresh harvest media (designated the "low activity form" of rhASM) and a second preparation was made from media that had been stored at −20° C. for 3 months (designated the "high activity form" of rhASM). Activity measurements of the purified rhASM from these two preparations indicated a substantial difference in specific activity for the two: 17.3 U/mg for the preparation from fresh harvest versus 80.2 U/mg for the preparation from harvest stored at −20° C. Thus, purified enzyme from harvests stored at −20° C. has approximately 5-fold higher specific activity than enzyme purified from fresh harvests.

A kinetic analysis of these two "forms" of rhASM was conducted. Recombinant-human-ASM (rhASM) was incubated at 37° C. with an excess (12.5 mM) of 2-(N-hexadecanoylamino)-4-nitrophenylphosphorylcholine (CalBiochem, San Diego, Calif.) in 250 mM sodium acetate, pH 5.5 containing 0.1 mM zinc acetate, 0.25 mg/mL BSA, and 0.15% Tween 20. After a 30 minute incubation at 37° C., 0.2 M Glycine-NaOH containing 50% ethanol was added to stop the reaction. Activity was determined by calculating the amount of cleaved substrate (2-(N-hexadecanoylamino)-4-nitrophenolate) produced during the reaction ($\epsilon_{415}$=15.0 $mM^{-1}cm^{-1}$). In activity assays designed to determine metal-ion dependence, rhASM was diluted in the same buffer but with no metal ions present. Various amounts of divalent metal ions were then added to the samples for a 30 minute pre-incubation at 37° C. prior to the addition of 2-(N-hexadecanoylamino-4-nitrophenylphosphorylcholine substrate which was made in no-metal buffer. Kinetic parameters were assessed at 415 nm using varying concentrations of substrate, 2-(N-hexadecanoylamino)-4-nitrophenylphosphorylcholine, in 250 mM sodium acetate, pH 5.5 containing 0.1 mM zinc acetate, 0.25 mg/mL BSA, and 0.15% Tween 20. Kinetic parameters were determined from Eadie-Hofstee plots of the resulting data.

TABLE I

Kinetic analysis of high and low activity ASM proteins.

| rhASM protein | $K_M$, mM | Vmax, U/mg |
|---|---|---|
| Low-activity form | 1.7 | 21.1 |
| High-activity form | 1.9 | 92.8 |

EXAMPLE 3

DTNB Activity Assay

Samples of low-activity and high-activity forms of rhASM were first concentrated in 20 mM sodium citrate, 150 mM NaCl, pH 6.0. Free thiol content was assessed at 412 nm using 0.8-1.2 mg rhASM and 0.5 mM DTNB in native and denaturing buffers and incubated for 10 minutes at room temperature before reading absorbance values. Results were compared to a cysteine standard curve. The results established that the low-activity form of rhASM contained one free thiol, whereas the high-activity form contained no free thiols.

EXAMPLE 4

Chemical Modification of rhASM Free Thiol Using Methyl Methane Thiosulfonate (MMTS) and Oregon Green® Maleimide (OGM)

Figure 1:
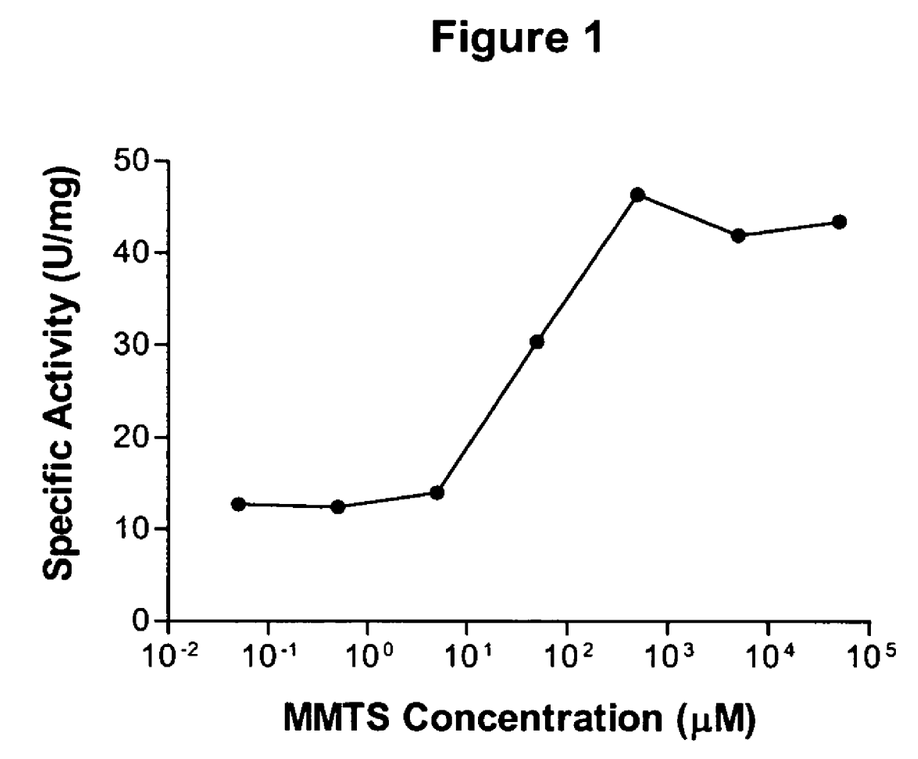
FIG. 1 is a graph illustrating the specific activity of thiol-modified rhASM as a function of methyl methanethiosulfonate (MMTS) concentration. Samples were subjected to a standard ASM activity assay.]

As the loss of the free cysteine appeared to correlate with increased activity, based on the high and low activity preparations, experiments were carried out to test whether rhASM activation could be achieved by chemically blocking the thiol group of the free cysteine residue in the low activity form. A small molecular weight modifier of thiols, MMTS modifies cysteine to form a mixed disulfide bond (S—S—$CH_3$). Due to its small size, it is among the least perturbing cysteine-modification regents available for protein structure function studies. The low activity form of rhASM was subjected to modification by MMTS and its activity subsequently measured using the standard activity assay (see FIG. 1). As indicated in FIG. 1, increasing the amount of MMTS (and thus increasing the extent of modification) resulted in increases to the specific activity of rhASM, with a maximal increase of about 5-fold.

OGM was also used to modify free cysteine on the low activity form of rhASM. OGM represents a larger molecular weight modifier that, unlike MMTS modification, is irreversible. It also acts as a fluorescent tag to allow tracking of the modification. OGM modification resulted in increases to the specific activity of rhASM very similar to that observed with MMTS modification. This indicates significant flexibility in the nature of the modification and the size of the modifier.

To identify the position of the free cysteine in rhASM that is involved in this activation, 0.5 mg of OGM-modified rhASM was prepared for peptide mapping and characterization. The rationale was to take advantage of the absorbance/fluorescence properties of Oregon Green® 488 to identify cysteine-labeled peptide(s) within the peptide maps. Peptides from a trypsin digestion were separated on a C4 reverse-phase HPLC column and the elution of OGM-labeled peptides was monitored by absorbance at 495 nm. Only one major peak was detected in the peptide map at this wavelength, consistent with the DTNB result indicating only one free cysteine in the protein. This peak was collected and analyzed by MALDI-TOF mass spectrometry. The results indicated that the free cysteine was present in the C-terminal tryptic peptide of rhASM To further confirm that it is the C-terminal peptide that was modified, post-source decay (PSD) fragmentation was carried out on the MALDI-TOF target with the labeled peptide peak. The results clearly identified the C-terminal cysteine as the free cysteine that is modified by OGM.

EXAMPLE 5

Copper-Promoted Dimer Formation rhASM protein prepared as described above was dialyzed and diluted in 20 mM Tris-HCl, 150 mM NaCl, pH 7.0 to a final concentration of 0.5 mg/mL. $CuSO_4$ (0.1 mM unless specified otherwise) was added and the mixture was incubated at 37° C. for 30 minutes or on ice for one hour. In experiments designed to study disruption of the dimer, 100 mM DTT or 20 mM EDTA was added to the protein following copper treatment and the incubation was continued for an additional 30 minutes at 37° C. Incubated samples were analyzed by gel electrophoresis on a 4-20% pre-cast Tris-glycine gel (Novex) with Coomassie blue stain.

To understand the copper-dependent increase in activity, the two forms of the rhASM protein were incubated with 0.1 mM copper sulfate and examined on a 4-20% SDS-PAGE gel under non-reducing conditions. Copper incubation of the low activity form resulted in the appearance of a higher molecular weight band corresponding in size to a dimer of rhASM (130-140 kDa). Conversion of monomer to dimer did not occur in the copper-incubated high activity form. Therefore, copper enhances dimer formation in the low but not the high activity form. The dimer formed in this manner is sensitive to DTT as it disappeared when DTT was included in the loading buffer. This suggests the involvement of a disulfide bond in the dimer; and that copper promotes the formation of this intermolecular disulfide bond. This is consistent with the common practice in protein refolding experiments where copper ions are added to promote intra-molecular disulfide bond formation. The minimum concentration of copper required for rhASM dimer formation was ~10 mM.

EXAMPLE 6

Carboxypeptidase Y Treatment

Carboxypeptidase Y (CPY, obtained from Roche Molecular Biochemicals) was used to cleave amino acids from the C-terminus of the rhASM protein. Various ratios of CPY to rhASM (1:1 to 1:260,000) were combined in 20 mM Citrate, 200 mM NaCl, pH 6.0 buffer and incubated on ice for 8 hours. The samples were then subjected to activity assay and fluorescent labeling by OGM to measure the remaining free cysteine. Labeled rhASM was analyzed by SDS-PAGE on a 4-20% gel and visualized on a fluorescence reader (FACE imager from GLYKO, inc.) to quantify the intensity of the bands. The CPY reaction was also carried out using immobilized CPY beads (Pierce) to confirm the results from the solution digest. Briefly, aliquots of 1 mg/mL rhASM (0.1 mL) were mixed with 10 μL of the CPY beads on top of a 0.45 μm spin filter (Ultrafree-MC from Millipore). The digested protein was spun through the filter to remove the immobilized CPY at various time points and the filtrate was then assayed for ASM activity.

Figure 2:
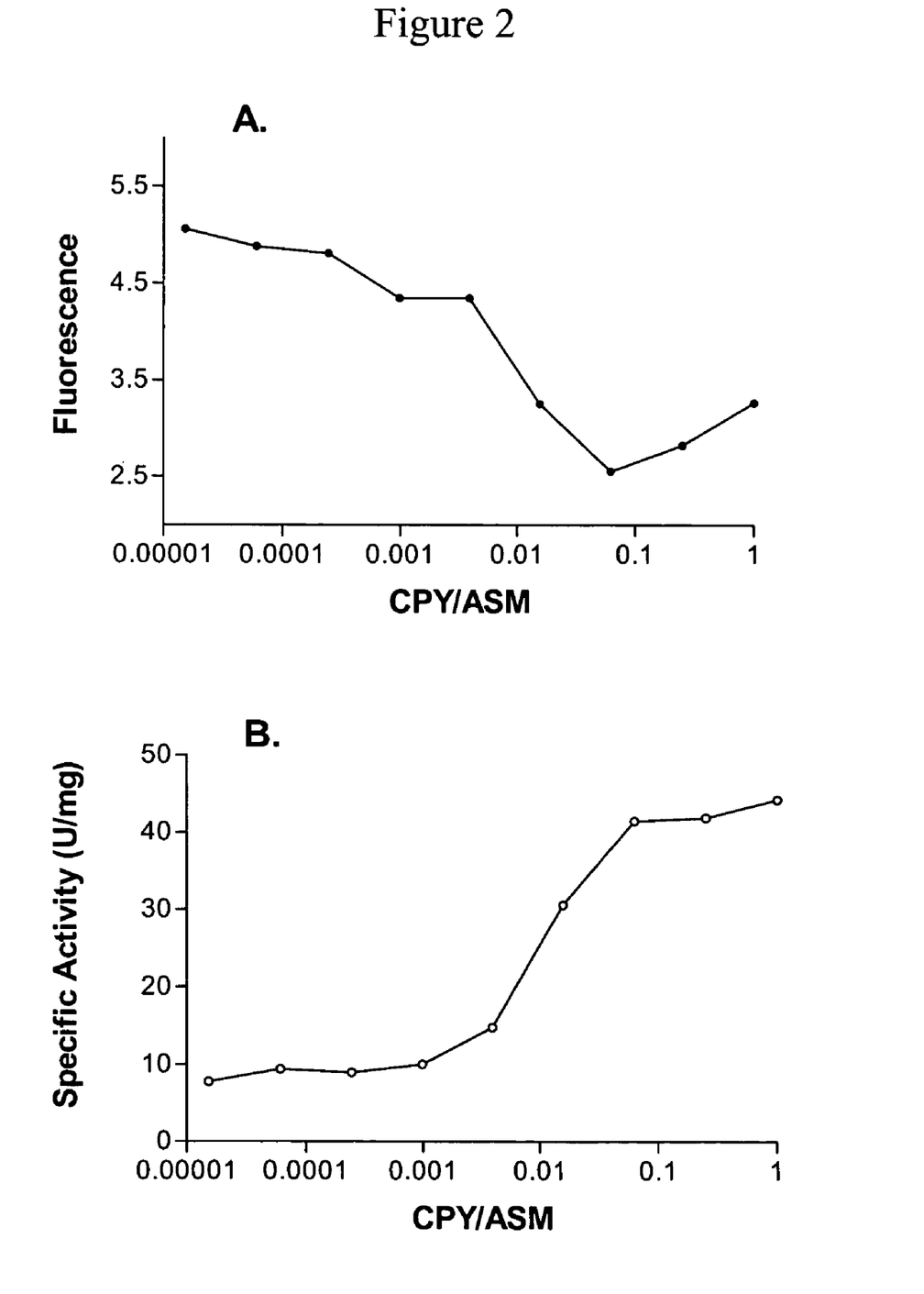
FIG. 2A shows the levels of fluorescence detected from bands of OGM-treated samples analyzed by SDS-PAGE.
FIG. 2B shows the ASM activity of the CPY treated samples for the solution reaction.

Carboxypeptidase Y (CPY) cleaves amino acids sequentially from the C-terminal end of proteins. Since the labeling results described above indicated that it is the C-terminal free cysteine that is responsible for activation of rhASM, CPY treatment was performed to see whether removal the C-terminal cysteine also results in activation of rhASM. The low activity form of rhASM was incubated with CPY at different enzyme-to-protein ratios, and the activity was monitored for each reaction. The loss of C-terminal cysteine was monitored in this experiment by the susceptibility of the protein to OGM labeling. CPY-digested samples were incubated with OGM before loading onto a 4-20% SDS-PAGE to determine the degree of OGM labeling. The intensity of the fluorescence band for each reaction was quantitated as described in Experimental Procedures (FIG. 2A). Clearly, rhASM gradually loses the ability to be labeled by OGM as the CPY concentration is increased, reflecting the loss of the C-terminal free cysteine. Activity measurements showed that rhASM activity increases as more CPY is used in the incubation (FIG. 2B). In parallel with this digestion using soluble CPY, an incubation time course using immobilized CPY was also performed, and a similar pattern of rhASM activation was observed (data not shown). These results indicate that enzymatic deletion of the C-terminal cysteine results in activation of rhASM, consistent with the conclusion from the thiol modification data.

EXAMPLE 7

Substitution of $CYS^{629}$

The ASM cDNA was obtained from the IMAGE Consortium (GenBank Accession AI587087). The open reading frame was amplified by PCR utilizing reverse primers in which the terminal cysteine codon, TGC, was either deleted or mutated to TCC (serine). PCR products were cloned into mammalian expression vectors containing a DHFR selectable marker. Plasmids were sequenced through the entire open reading frame to confirm that only the desired mutation was present. DHFR deficient CHO-DXB11 cells were transfected using lipofectamine (Gibco) and selection was carried out in nucleotide deficient media supplemented with 10% dialyzed FBS and 0.2 FM methotrexate (CalBiochem). Recombinant ASM expression levels were further boosted by subjecting the uncloned pools to incremental increases in methotrexate concetration.

From the data described above, it appears that either modification or deletion of the C-terminal cysteine leads to a substantial increase in the activity of rhASM. To confirm the role of the C-terminal cysteine in this activation, site-directed mutagenesis was carried out to generate ASM mutants in which the C-terminal cysteine ($Cys^{629}$) is either eliminated by substitution with a stop codon ($Cys^{670}$del) or mutated to serine ($Cys^{629} \rightarrow Ser$). The mutant proteins were over-expressed in stably-transfected CHO cells and purified. The specific activity of the purified mutant forms was measured and compared to the wild-type full-length rhASM protein (Table II). Both mutants displayed an average increase of about 5-fold in specific activity compared to the full-length wild-type form. These results confirm the conclusion that modification or deletion of the thiol group on the C-terminal cysteine leads to activation of ASM.

TABLE II

Activity of wild-type (WT) and mutant rhASM proteins.

| rhASM Protein | Specific Activity (U/mg) | Fold Activation |
| --- | --- | --- |
| Wild Type | 17.3 | 1.0 |
| $Cys^{629}$del | 85.3 | 4.9 |
| $Cys^{629} \rightarrow Ser$ | 91.1 | 5.3 |

While this invention has been particularly shown and described with references to preferred embodiments thereof, it will be understood by those skilled in the art that various changes in form and details may be made therein without departing from the scope of the invention.

---

We claim:

1. A method of increasing the activity of human acid sphingomyelinase enzyme (ASM) comprising modifying the C-terminal cysteine amino acid residue of human ASM wherein said human ASM corn rises the amino acid seoucuce of SEQ ID NO: 1 or the amino acid sequence which starts at His$^{60}$ and ends at Cys$^{629}$ of SEQ ID NO: 1, and said modification causes the loss of activity of the free thiol group in said cysteine residue thereby increasing the acid sphingomyelinase activity of said ASM.

2. The method of claim 1 wherein said modification comprises a deletion of the C-terminal cysteine amino acid residue.

3. The method of claim 1, wherein said modification comprises a substitution of said C-terminal cysteine amino acid residue.

4. The method of claim 3, wherein said C-terminal cysteine amino acid residue is substituted with serine, threonine or alanine.

5. The method of claim 3, wherein said C-terminal cysteine amino acid residue is substituted with a serine amino acid residue.

6. The method of claim 1, wherein said modification comprises a dimerization of said ASM.

7. The method of claim 6, wherein said ASM dimer is cross-linked with a disulfide bond.

8. The method of claim 1, wherein said modification comprises the attachment of a compound to said C-terminal cysteine amino acid residue.

9. The method of claim 8, wherein said compound comprises a thiol protecting group.

10. The method of claim 9, wherein said thiol protecting group is selected from the group consisting of a thioether, a thioester, and an unsymmetrical disulfide.

11. The method of claim 8, wherein said compound comprises a modifier of cysteme.

12. The method of claim 11, wherein said modifier of cysteine is an irreversible modifier.

13. The method of claim 12, wherein said irreversible modifier is maleimide.

14. A method of increasing the acid sphingomyelin activity of human ASM comprising modifying the C-terminal cysteine residue of human ASM wherein said human ASM comprises the amino acid sequence of SEQ ID NO: 1 or the amino acid sequence which starts at His$^{60}$ and ends at Cys$^{629}$ of SEQ ID NO: 1, and the modification is selected from the group consisting of:
  (a) deletion of the C-terminal cysteine residue;
  (b) substitution of the C-terminal cysteine residue with another amino acid residue;
  (c) dimerization of the ASM; and
  (d) attachment of a compound to the C-terminal cysteine residue, wherein said modification causes the loss of activity of the free thiol group in the cysteine residue thereby increasing the acid sphingomyelin activity of said ASM.

* * * * *

UNITED STATES PATENT AND TRADEMARK OFFICE
CERTIFICATE OF CORRECTION

PATENT NO. : 7,527,956 B2 Page 1 of 1
APPLICATION NO. : 10/864981
DATED : May 5, 2009
INVENTOR(S) : Scott M. Van Patten, Kenneth P. Karey and Huawei Qiu It is certified that error appears in the above-identified patent and that said Letters Patent is hereby corrected as shown below:

Claim 1, Column 23, line 40: Delete "corn rises" and insert --comprises--

Claim 1, Column 23, line 40: Delete "seoucuce" and insert --sequence--

Claim 11, Column 24, line 42: Delete "cysteme" and insert --being cysteine--

Signed and Sealed this

Fourteenth Day of July, 2009

JOHN DOLL
*Acting Director of the United States Patent and Trademark Office*